United States Patent [19]

Braatz

[11] 4,266,573
[45] May 12, 1981

[54] ANESTHESIA MACHINE HAVING PROPORTION LIMITING CONTROL SYSTEM

[75] Inventor: Robert E. Braatz, Sun Prairie, Wis.
[73] Assignee: Airco, Inc., Montvale, N.J.
[21] Appl. No.: 86,961
[22] Filed: Oct. 19, 1979
[51] Int. Cl.³ ............................................. A61M 17/00
[52] U.S. Cl. ............................ 137/630.18; 128/203.25; 137/607; 251/294
[58] Field of Search .............. 137/607, 630.18, 630.19, 137/635; 128/203.12, 203.23, 203.24, 203.25; 251/294

[56] References Cited

U.S. PATENT DOCUMENTS

| | | | |
|---|---|---|---|
| 400,177 | 3/1889 | Bell | 137/607 X |
| 748,763 | 1/1904 | MacFadden | 137/607 X |
| 892,155 | 6/1908 | Hodges | 137/607 X |
| 1,175,881 | 3/1916 | Creelman | 137/607 |
| 1,793,608 | 2/1931 | Gramberg | 128/203.25 X |
| 3,534,753 | 10/1970 | Ollivier | 137/88 X |
| 3,717,177 | 2/1973 | Glesmann | 137/607 |
| 3,739,799 | 6/1973 | Bickford | 137/88 |
| 3,809,109 | 5/1974 | Breiling | 137/607 |
| 4,191,952 | 3/1980 | Schreiber | 128/203.25 X |

Primary Examiner—Robert G. Nilson
Attorney, Agent, or Firm—Roger M. Rathbun; Larry R. Cassett

[57] ABSTRACT

A system is disclosed for providing an interconnection between two needle valves such that movement of either needle valve, in opening or closing thereof, is affected or limited by movement of the other valve. The invention is particularly suited to an anesthesia machine wherein separate supplies of oxygen ($O_2$) and nitrous oxide ($N_2O$) are fed to individual needle valves which are then individually adjusted to provide a desired mixture of $N_2O$ and $O_2$ for administration to a patient to anesthetize the same. The system herein disclosed interconnects the individual needle valves such that the $O_2$ needle valve may be opened fully without restriction, however, when the $N_2O$ valve is open, the interconnection provides that closing of the $O_2$ valve will, at a predetermined point, also correspondingly close the $N_2O$ valve, thus preventing the percentage of $N_2O$ in the mixed gas from raising above a set value, i.e. one at which sufficient oxygen for a respirable mixture is assured. Similarly, the $N_2O$ valve is prevented, through the same interlock system, from being opened beyond a point where the $N_2O$ percentage could exceed such limit. Again, when the $N_2O$ valve reaches the predetermined point, further opening of the $N_2O$ valve also opens the $O_2$ valve such that the flow can be increased by further opening of the $N_2O$ valve but the percentage of $N_2O$ and $O_2$ will thereafter remain constant. In addition, the overall system has a further preventative feature where the flow of oxygen cannot be set below a predetermined value so that sufficient oxygen flow to the patient is assured.

7 Claims, 3 Drawing Figures

ANESTHESIA MACHINE HAVING PROPORTION LIMITING CONTROL SYSTEM

BACKGROUND OF THE INVENTION

This invention relates to an anesthesia machine, and more particularly, to a machine adapted to receive separate supplies of oxygen and nitrous oxide and to cause mixing thereof to dispense a mixture of oxygen and nitrous oxide for anesthetizing a patient. The machine is provided with the capability of varying the relative proportion of the individual gases in the final mixture yet an interlocking system prevents certain mixtures being selected, even inadvertently, by the user.

One very common means of inducing anesthesia in patients is the combination of oxygen and nitrous oxide. For certain dental procedures, that mixture alone may give sufficient anesthesia, while in more serious surgical operations, the mixture may be used for induction followed by administration of more potent inhalant anesthetics such as enflurane, marketed under the trademark Ethrane.

There are, therefore, various different techniques and corresponding apparatus for mixing the two components, oxygen and nitrous oxide, to evolve a mixture that may vary in proportions over a range.

One typical arrangement is to provide two needle valves, one of which receives oxygen and the other of which receives the nitrous oxide. Both gases are available in hospitals through built-in piping systems, or in the alternative and in the event of any failure of such piping systems, supplies are readily available commercially in cylinders. While the use of individual needle valves to provide the respirable mixture is relatively simple in operation and components, it does suffer from a potential safety problem in that a user could inadvertently create a mixture having too low a percentage of oxygen in such mixture. As is well known, the oxygen percentage in the inspired gases should not fall below about 21% by volume. Also, there must be a minimum flow of oxygen to the patient in order to meet the metabolic requirement of the patient.

Other devices have been marketed, such as shown in U.S. Pat. Nos. 3,717,177 to Glesmann and 3,739,799 to Bickford et al, however, such devices, while acceptable to maintain oxygen ratios, are generally quite complex to construct and thus are relatively expensive. In addition, they are not readily accepted by many users that are accustomed to the more conventional technique of adjusting individual needle valves to obtain the desired mixtures.

SUMMARY OF THE INVENTION

Now, in accordance with the present invention, a gas mixing system, particularly adapted for use as an anesthesia machine, is described which provides great flexibility for the operation in selecting various flows and/or mixture concentrations of $O_2$ and $N_2O$ and yet which is relatively inexpensive and is similar, in outward appearance, to the present needle valve-flowmeter systems that are familiar to most anesthesiologists. Yet, the system eliminates the troublesome difficulty of maintaining a minimum $O_2$ flow and $O_2$ concentration in the mixed gases, such that the operator can feel at ease that the gases delivered to the patient will sustain respiration.

The system includes flowmeters for a visual indicator of the individual flows of $O_2$ and $N_2O$ and also comprises individual needle valves that are operable to control the flow of the individual gases so that the overall relative proportions of $O_2$ and $N_2O$ in the resultant mixture can be readily set by the operator.

A built-in safety system is described wherein the individual needle valves for $O_2$ and $N_2O$ are interconnected, that is, control or movement of one valve will, at times, also have an effect on the other valve.

Specifically, a linking means is used between the two needle valves. As the $N_2O$ needle valve is opened, it may move freely until it reaches a predetermined point where the combined mixture of $O_2$ and $N_2O$ would result in the proportion of $N_2O$ advancing above 79%. At that point, the linking means opens the $O_2$ needle valve as the $N_2O$ valve is further opened and further opening of the $N_2O$ valve will increase the flow of gases but the proportion of $N_2O$ will remain constant at 79%. Thus, the $N_2O$ valve cannot be opened to any point where the percentage of $O_2$ in the mixture falls below 21%. The $N_2O$ valve can be freely closed further without its moving the $O_2$ needle valve, or the $O_2$ needle valve could be further opened without affecting the $N_2O$ valve since either action would not serve to further lower the $O_2$ concentration in the mixture from the system. But, reverse movement of either valve would bring the linking means into play, that is, once the minimum concentration is established between the two valves, any attempt to close the $O_2$ needle valve or open further the $N_2O$ valve automatically links up with the other valve causing, respectively, closing of the $N_2O$ valve and opening of the $O_2$ valve such that the minimum 21% of $O_2$ in the mixture is maintained. No valve movement of either the $O_2$ or $N_2O$ valve can cause the $O_2$ concentration in the final mixture to be reduced below 21%.

In addition, precision of desired concentrations and changes thereof by needle valve movement is assured by spring loading the needle valve movable members and providing fixed bearings. This movement of the valve is positive and precise and, therefore, the change in valve opening corresponding to a predetermined rotational movement of the movable valve member is extremely predictable.

DESCRIPTION OF THE DRAWINGS

The invention is diagrammatically illustrated by way of example, in the drawings appended hereto, in which.

DETAILED DESCRIPTION OF THE INVENTION

Figure 1:
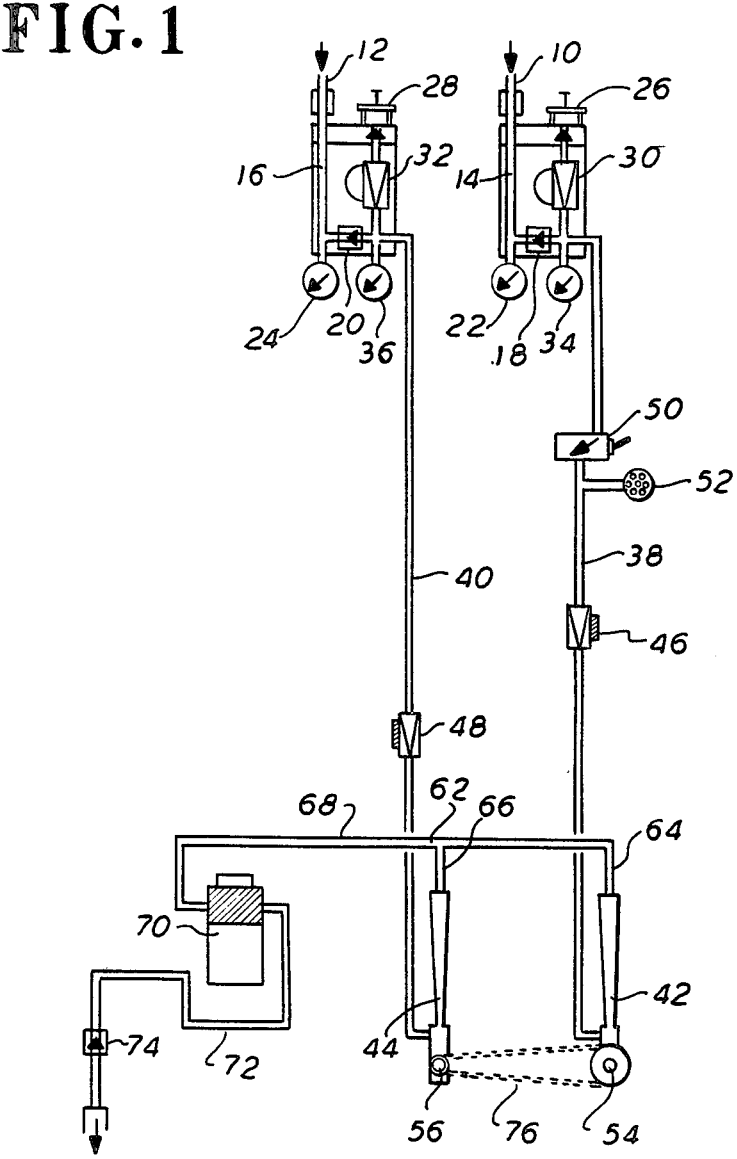
FIG. 1 is a schematic view of an anesthesia machine wherein mixing of two separate gases occurs.

Referring particularly to FIG. 1, there is shown a schematic view of an anesthesia machine adapted to provide a mixture of oxygen and nitrous oxide to a patient for inducing anesthesia.

The machine includes an oxygen inlet 10 and a nitrous oxide inlet 12 which are adapted to be connected to normal pipelines of those gases supplied in a hospital. Such pipeline systems are readily used in hospitals having typical pressures for both nitrous oxide and oxygen of about 50 psi.

The gases, oxygen and nitrous oxide thus pass respectively through suitable inlet tubes 14, 16 and check valves 18, 20 and the pressure in each of the pipelines can be read by gages 22 and 24.

In the event pipeline gases encounter a failure, or in some instances where pipeline gases are not availble, a suitable yoke for oxygen and nitrous oxide, 26 and 28 are adapted to receive gas cylinder which is then regulated by regulators, respectively 30 and 32, and pressure indicated by gages 34 and 36.

Main conduits 38 and 40 feed, respectively, the oxygen and nitrous oxide to flowmeters 42 and 44 where a visual indication of the flow of the two gases may be continuously monitored by the user.

Pressure regulators 46 and 48 are located in the conduits 38 and 40 and further, in the oxygen conduit 38, there may also be a main oxygen shutoff valve 50 and an indicator 52 which notifies the user whenever the machine is on.

Carrying out the remaining components of the anesthesia machine, at the inlets to the oxygen flowmeter 42 and the nitrous oxygen flowmeter 44 are needle valves, respectively 54 and 56 which are normally adjusted by the user to choose whatever end proportions of nitrous oxide and oxygen are desired in the eventual mixture. The user is, of course, guided in such adjustment by the visual monitoring of the flow of each of the gases by the individual flowmeters 42 and 44.

The gases from the flowmeters 42 and 44 mix in a confluence at 62 when tubes 64 and 66 meet, each carrying its particular gas.

The mixed gas of nitrous oxide and oxygen continues through tubing 68 into a typical vaporizer 70 where a potent liquid anesthetic may be picked up and thus carried by the gas stream in the form of vapor through an outlet tubing 72, through a check valve 74 and thereafter is administered to the patient.

Thus far, a conventional anesthesia machine has been described, however, in FIG. 1, there is further shown a chain 76 which forms a connection between the oxygen needle valve 54 and the nitrous oxide needle valve 56. This chain 76 is a part of the proportion limiting system of the present invention, and its purpose and function will be later explained.

Figure 2:
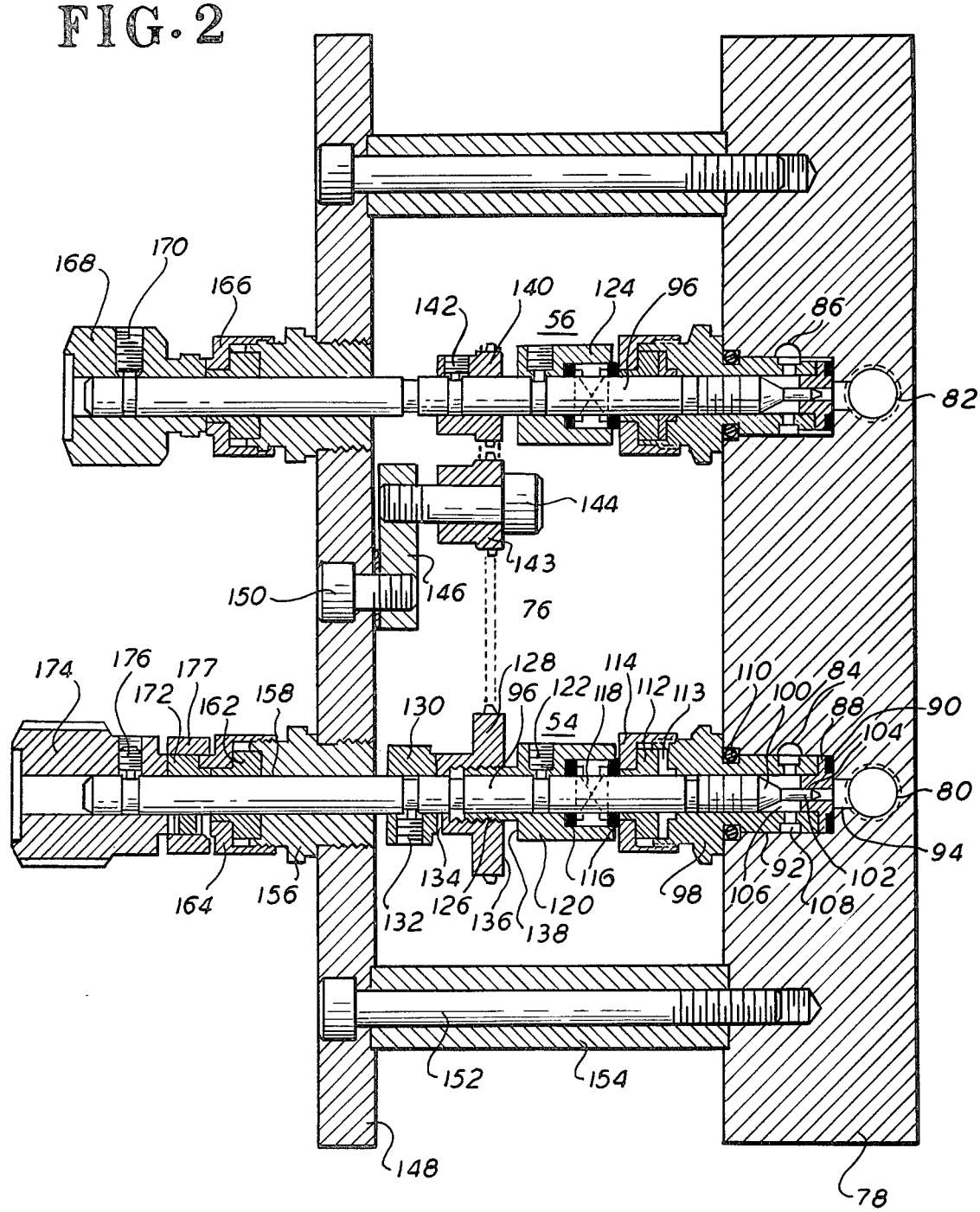
FIG. 2 is a side cross-sectional view of the proportion limiting system of the present invention.

Turning now to FIG. 2, there is shown a top cross-section of the anesthesia needle valves 54 and 56 for, respectively, oxygen and nitrous oxide. The needle valves 54 and 56 are mounted on a manifold 78 by a threaded engagement. Also formed in the manifold 78 are a pair of inlets 80, 82 through which oxygen and nitrous oxide are, respectively, introduced to the needle valves for control of such gases. Suitable outlets 84 and 86 are also formed in the manifold 78 and which convey the oxygen and nitrous oxide, respectively, from the needle valves 54 and 56 to the flowmeters 42 and 44 (FIG. 1).

Basically, the major components of the needle valves 54 and 56 are of conventional design and, for purposes of this disclosure, the description will set forth the working components of only the oxygen needle valve 54 where the same components are found in the nitrous oxide needle valve 56.

Taking the oxygen needle valve 54, the forward portion forms a seat 88 that seals against an O-ring 90 within the threaded hole 92 in the manifold 78. A transverse hole 94 receives the oxygen from inlet 80 to communicate the same with the needle valve 54.

The valve stem 96 is threaded within stud 98 and therefore, when rotated, moves laterally within stud 98, the stud 98 being fixed with respect to the manifold 78.

At the forward end of the valve stem 96, i.e. toward manifold 78, there is formed a tip 100 which is of a cylindrical tapered configuration, the reduced diameter portion 102 of the tip fits within a slightly tapered hole 104 within the valve seat 88.

As the oxygen enters the needle valve 54 from the transverse hole 94, therefore, it passes through the tapered hole 104 and the flow of such gas depends upon the position of the reduced diameter portion 102 of tip 100. As that portion 102 is withdrawn, obviously, the flow of oxygen through the tapered hole 104 is increased. As the gas passes through the tapered hole 104, it enters a chamber 106 and passes outwardly through a plurality of radial holes 108 to the outlet 84.

The stud 98 is sealed against the manifold 78 when it is affixed thereto by means of O-ring 110. At the other, external end of the stud 98 there is a bearing 112 which retains the valve stem 96 and compresses a gasket 113 against the stud 98 to form a seal therebetween by means of the axial load imposed by nut 114.

Backlash is eliminated in the valve movement by means of a pair of thrust washers 116 which are separated by a compression spring 118. The washers 116 fit within sleeve 120 which is secured to the valve stem 96 by means such as a set screw 122. By the positioning of the sleeve 120 on valve stem 96, the compression spring 118 causes a force exerted outwardly by the thrust washers 116, one of which produces the force against nut 114 which is fixed with respect to stud 98 and the other of which produces a force against the internal surface of the sleeve 120 forcing the same outwardly and preventing slack or backlash in the rotational movement of the valve stem 96 within the stud 98.

As may be seen in FIG. 2, the sleeve 120 for the oxygen needle valve 54 is shaped differently than the corresponding sleeve 124 for the nitrous oxide needle valve 56. Both function in the same manner for eliminating backlash in the movement of the valve stems 96, however, the sleeve 120 for oxygen needle valve 54 also performs an additional function in achieving the proportion limiting feature of the present invention.

In particular, the sleeve 120 has an externally threaded extension 126, upon which is mounted a sprocket 128 having its internal bore threaded correspondingly to the external threads of extension 126 such that rotation of either the sleeve 120 or the sprocket 128 with respect to each other causes lateral movement between the sleeve 120 and sprocket 128. A stop 130 is also mounted on the oxygen needle valve stem 96 and is positioned in a predetermined location on the stem 96 for purposes which will later become apparent. The stop 130 may be secured to the valve stem 96 by means such as a set screw 132.

As may now be seen, the sprocket 128 may freely move along the threaded extension 126 within a specific lateral distance before it meets some constraint. In the event of movement toward the stop 130, the sprocket 128 may move laterally until the stop 130 is engaged by an outward projection (not shown) on surface 134 of sprocket 128 which engages an outward projection (not shown) on stop 130. In the event of lateral movement in the opposite direction, the sprocket moves laterally along the threaded extension 126 until its surface 136 almost touches the shoulder 138 formed in the sleeve 120.

Another sprocket 140 is firmly affixed to the valve stem 96 of the nitrous oxide needle valve 56. This sprocket 140 is held to the stem 96 by means such as set screw 142 and therefore moves with the stem 96 as it is rotated to change the valve position. A further sprocket 143 is provided intermediate sprockets 128 and 140 and is held in position by a cap screw 144 and provides a tensioning means for the chain 76 to insure proper tension. A linkage 146 provides the tension by being tightened into a predetermined position, and the linkage 146 is, in turn, affixed correspondingly to a front plate 148 of the anesthesia machine.

Suitable means are provided to retain the front plate 148 firmly in position with respect to manifold 78 and, as shown, such means may include cap screws 152 which are threaded into the manifold 78 and which secure the correct distance between the front plate 148 and manifold 78 by spacers 154.

On the front plate 148, there is mounted, by threaded engagement therewith, a guide 156 having an internal bore 158 through which the valve stem 96 is carried and is movable therein.

A bearing 162 is retained in position by a nut 164 which is securely screwed to the guide 156. The bearing 162 acts along with bearing 112 to prevent wobble of the valve stem 96. A similar construction of components on the front plate 148 is evident with respect to the nitrous oxide needle valve 56 with the exception that the nut 166 for valve 56 is slightly different than the corresponding nut 164 as will be later explained.

Completing the description of the nitrous oxide valve 56, an operating knob 168 is affixed to the end of the valve stem 96 by set screw 170 and thus, an operator can readily grasp and turn knob 168 to change the desired setting of the nitrous oxide needle valve 56. In addition, as the nitrous oxide needle valve 56 reaches the closed position, a small outward projection (not shown) on knob 168 and facing nut 166 engages a similar outward projection (not shown) on the nut 166 and facing knob 168 such that further rotation of knob 168 in the closing direction is prevented.

A cylindrical sleeve 172 encircles the oxygen needle valve stem 96 outwardly of nut 164 and sleeve 172 has an internal bore that enables it to rotate freely about the valve stem 96. A knob 174 is positioned at the end of the oxygen valve stem 96 and is affixed thereto and rotates therewith by means such as set screw 176. A cylindrical cover 177 encircles sleeve 172 and affords protection thereto against dirt, etc. that could impair the function of sleeve 172.

Figure 3:
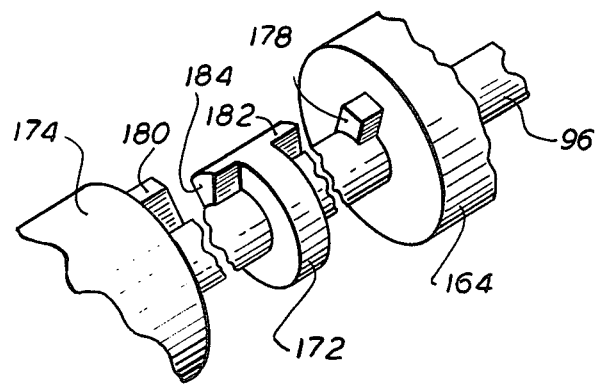
FIG. 3 is an enlarged isometric view of a portion of one of the gas valves used in the system.

The purpose of cylindrical sleeve 172 may be seen by reference to FIG. 3. As shown on FIG. 3, the nut 164 for oxygen needle valve 54 has an outward projection 178 and the knob 174 has a similar outward projection 180.

Cylindrical sleeve 172 has two such outward projections, shown as 182 and 184, both of which are about oppositely disposed and one of which faces the outward projection 178 of nut 164 and the other of which faces the outward projection 180 of knob 174.

As shown in FIG. 3, outward projections 182 and 184 of sleeve 172 do not contact or engage the outward projection 178 or the outward projection 180, however, in actual use, the knob 174 and nut 164 are closer together such that at no time can the sleeve 172 be rotated without one of its outward projections 182 and 184 engaging the respective outward projections 178 and 180 of the nut 164 and the knob 174, respectively.

Accordingly, in operation, the sleeve 172 serves to provide a limit for rotational movement of the knob 174 and thereby the valve stem 96, in both a clockwise and counterclockwise direction. As an example, if the know 174 is rotated clockwise, it moves towards the nut 164 as oxygen needle valve 54 progresses towards the closed position. At the point of minimum flow desired for oxygen, the outward projection 182 of sleeve 172 engages outward projection 178 of nut 164 and at the same time, the outward projection 184 of sleeve 172 engages outward projection 180 of the knob 174, thus preventing further rotational movement of the valve stem 96 in the clockwise direction and establishing a minimum flow of oxygen. This value (minimum flow) is determined by the size of the outward projections concerned, as well as with the thread pitch of the needle valve.

Similarly, as knob 174 is turned counterclockwise, thereby opening the oxygen needle valve 54, the knob 174 can be rotated about two complete revolutions or approximately 720° before the outward projections 182 and 184 of sleeve 172 again engage, respectively, outward projection 178 of nut 164 and outward projection 180 of knob 174, thus preventing further counterclockwise rotation of knob 174 and correspondingly preventing further opening of the needle valve 54. In such manner, the maximum opening of needle valve 54 is also established.

The operation of the proportion limiting system of the present invention can now be described, particularly with reference to FIGS. 2 and 3.

The minimum flow rate for oxygen as determined by oxygen needle valve 54 is established, as previously stated, by adjusting the position of the nut 164 such that its outward projection 178 is held in a predetermined position. In such position, the valve stem 96 may be rotated to attain that minimum oxygen flow desired and the knob 174 firmly set in position at that point by tightening the set screw 176. This setting automatically determines the minimum flow of oxygen, and, because the outward projections 182 and 184 on the sleeve 172 limit the counterclockwise or outer movement of valve stem 96, a maximum flow is also established for oxygen. Again, this maximum flow is determined by the pitch of the threads of needle valve 54 as well as the size of the outward projections.

The nitrous oxide needle valve 56 is set by closing the same and then affixing know 168 in the closed position, where the outward projections of knob 168 and nut 166 abut each other, by tightening the set screw 170. In such closed position the sprocket 140 may be rotated clockwise (in the closing direction of needle valve 56) until the surface 136 of sprocket 128 almost touches shoulder 138 of sleeve 120. At this position the set screw 142 is tightened.

As to the proportioning system, the chain 76 creates a dependency, to a certain extent, of the movement of one valve to the movement of the other valve.

Taking an example, when the operator desires to administer nitrous oxide to a patient, the minimum oxygen flow already having been established, the knob 168 is turned counterclockwise, thus advancing the valve stem 96 and opening the nitrous oxide needle valve 56. As the nitrous oxide valve 56 opens, pulley 140 also turns counterclockwise and through the chain 76, pulley 128 also turns counterclockwise.

The turning of pulley 128 causes it to rotate on its threads on threaded extension 126 and, since they are both right hand threads, pulley 128 advances laterally with respect to the valve stem 96. At a predetermined ratio of nitrous oxide and oxygen, pulley 128 will have its outward projection on surface 134 engage the facing outward projection on stop 130. At this point, further opening of the nitrous oxide needle valve 56 also causes opening of the oxygen needle valve 54, thus, the proportion of nitrous oxide in the final mixture has reached a maximum, i.e. 76% for example. Further opening of the nitrous oxide needle valve 56 may increase the flow of the final mixture, but because there is a corresponding opening of the oxygen needle valve 54, the proportion of nitrous oxide in such mixture stays fixed.

At any time, however, the nitrous oxide needle valve 56 may be turned to the closed position and even closed entirely without moving or in any way changing the setting of the oxygen needle valve 54. Thus the operator is able to set any desired proportion of nitrous oxide in the final mixture, provided, however, the nitrous oxide has a maximum setting or proportion that cannot be exceeded.

As may also be seen, the oxygen needle valve 54 cannot be turned toward the closed position once the outward projections of sprocket 128 and the stop 130 are engaged without causing a corresponding closing of the nitrous oxide needle valve 56. Therefore, when the maximum proportion of nitrous oxide has been reached, the user cannot go above that proportion by either increasing the flow of nitrous oxide or by decreasing the flow of oxygen.

Obviously, any reasonable upper limit on the proportion of nitrous oxide, i.e. less than 79% or other gas may be set by moving the location of the stop 130, or by changing the pitch of the threads on threaded extension 126. Additionally, the sprocket ratio between sprockets 140 and 128 may be changed to control the ratio of flows of the two gases. Other factors could include the pressures at which the two agents are supplied; the lead of the threads of the valve stems 96 and the taper of the tapered hole 104 in the needle valves themselves.

Thus, although the invention has been shown and described specifically for an anesthesia machine wherein nitrous oxide and oxygen are the two gases being utilized, it may be easily seen that the proportion limiting system could be used for a range of other uses where a maximum limit on the proportion of one of such gases is desired, yet full flexibility afforded to select, within that range, any particular proportion of the gases.

It will be understood that the scope of the method and product of this invention is not limited to the particular steps or materials disclosed herein, by way of example, but only by the scope of the appended claims.

I claim:

1. An anesthesia machine for providing a mixture of oxygen and a second gas of selected proportions, said anesthesia machine having first and second rotatable valves, said first rotatable valve controlling the flow of oxygen and said second rotatable valve controlling the flow of the second gas, each of said rotatable valves being independently rotatable with respect to said other rotatable valve within a predetermined limit to vary the mixture of oxygen and the second gas, the improvement comprising interconnection means comprising a positive connection between said first and second rotatable valves such that rotation of said second rotatable valve toward its open direction is limited to a predetermined flow whereupon further opening also causes said first rotatable valve to open to prevent the percentage of oxygen by volume in the mixture provided by said machine to be below a predetermined percentage.

2. An anesthesia machine having a first needle valve for controlling flow of oxygen and a second needle valve for controlling flow of a second gas, means to supply each of said individual gases to said first and second needle valves, and means to mix said gases downstream of said first and second needle valves to produce a mixed gas of oxygen and the second gas, each of said first and second needle valves having, respectively, first and second rotatable stems for opening and closing said first and second needle valves, the improvement comprising a first sprocket affixed to said second rotatable stem of said second needle valve, and a second sprocket movable within predetermined limits of travel along the first rotatable stem of said first needle valve, and means interconnecting said first and second sprockets such that the movement of first and second sprockets are synchronized with respect to each other, whereby the rotation of said second needle valve toward the open direction causes said second sprocket to move to its predetermined limit of travel along the first rotatable stem of said first needle valve, whereupon further rotation of said second needle valve causes corresponding opening of said first needle valve.

3. An anesthesia machine for providing a mixture of oxygen and a second gas of selected proportions, said anesthesia machine having first and second rotatable needle valves, said first rotatable needle valve controlling the flow of oxygen and said second rotatable needle valve controlling the flow of the second gas, the improvement comprising a chain link interconnecting said needle valves, said chain link secured positively to said second rotatable needle valve and secured to said first rotatable needle valve with a predetermined amount of slippage wherein said predetermined amount of slippage allows limited rotation of said second needle valve towards its open position whereby further rotation of said second rotatable needle valve exceeding said predetermined slippage causes corresponding rotation of said first rotatable needle valve.

4. An anesthesia machine comprising oxygen inlet means adapted to receive a flow of oxygen gas, and second gas inlet means adapted to receive a flow of a second gas, said anesthesia machine having an outlet for delivering a mixed gas comprising oxygen and said second gas, a first valve for controlling the flow of oxygen to said outlet, a second valve for controlling the flow of said second gas to said outlet, said first valve and said second valve having, respectively, first and second valve shafts rotatable toward open and closed positions, and positive linkage means comprising a first sprocket affixed to said second valve shaft and a second sprocket threadedly engaged to and laterally movable along said first valve shaft, stop means affixed to said first valve shaft, a positive connection means coordinating rotation of said first and second sprockets, wherein movement of said second valve shaft and said first pulley toward the open position moves said second sprocket laterally along said first valve shaft to a predetermined position wherein said second sprocket engages said stop means, and after such engagement, said first valve shaft is caused to rotate toward its open position by further rotation of said second valve shaft toward its open position and said second valve shaft is caused to rotate toward its closed position by further rotation of said first valve toward its closed position such that the percentage of oxygen in the mixed gas cannot be reduced beyond a predetermined percentage.

5. An anesthesia machine as defined in claim 4 wherein said second gas is nitrous oxide.

6. An anesthesia machine comprising oxygen inlet means adapted to receive a flow of oxygen gas, and second gas inlet means adapted to receive a flow of a second gas, said anesthesia machine having an outlet for delivering a mixed gas comprising oxygen and said second gas, a first valve for controlling the flow of oxygen to said outlet, a second valve for controlling the flow of said second gas to said outlet, said first valve and said second valve having, respectively, first and second valve shafts rotatable toward open and closed positions, each of said valve shafts normally being independently rotatable with respect to the other of said valve shafts, and interconnection means between said first valve and said second valve, said interconnection means comprising stop means associated with said second valve shaft adapted to prevent further independent rotation of said second valve shaft toward its open position, said interconnection means causing rotation of said first valve shaft with further rotation of said second valve shaft toward the open position.

7. An anesthesia machine comprising oxygen inlet means adapted to receive a flow of oxygen gas, and second gas inlet means adapted to receive a flow of a second gas, said anesthesia machine having an outlet for delivering a mixed gas comprising oxygen and said second gas, a first valve for controlling the flow of oxygen to said outlet, a second valve for controlling the flow of said second gas to said outlet, said first valve and said second valve having, respectively, first and second valve shafts rotatable toward open and closed positions, each of said valve shafts normally being independently rotatable with respect to the other of said valve shafts, and interconnection means between said first valve and said second valve, said interconnection means comprising stop means associated with said first valve shaft adapted to prevent further independent rotation of said first valve shaft toward its closed position, said interconnection means causing rotation of said second valve shaft with further rotation of said first valve shaft toward the closed position.

* * * * *